(12) United States Patent
Lund et al.

(10) Patent No.: US 11,067,560 B2
(45) Date of Patent: Jul. 20, 2021

(54) SYSTEM FOR MEASURING MULTIPLE SOIL PROPERTIES USING NARROW PROFILE SENSOR CONFIGURATION

(71) Applicant: Veris Technologies, Inc., Salina, KS (US)

(72) Inventors: Eric Lund, Salina, KS (US); Chase Maxton, Salina, KS (US); Paul Drummond, Minneapolis, KS (US); Kyle Jensen, Salina, KS (US)

(73) Assignee: Veris Technologies, Inc., Salina, KS (US)

( * ) Notice: Subject to any disclaimer, the term of this patent is extended or adjusted under 35 U.S.C. 154(b) by 462 days.

(21) Appl. No.: 15/261,825

(22) Filed: Sep. 9, 2016

(65) Prior Publication Data

US 2017/0067869 A1  Mar. 9, 2017

Related U.S. Application Data

(60) Provisional application No. 62/216,087, filed on Sep. 9, 2015.

(51) Int. Cl.
*A01B 49/04* (2006.01)
*G01N 33/24* (2006.01)
(Continued)

(52) U.S. Cl.
CPC ......... *G01N 33/246* (2013.01); *A01C 21/007* (2013.01); *A01B 49/04* (2013.01); *A01C 5/062* (2013.01)

(58) Field of Classification Search
CPC ............. A01B 49/04; G01N 2033/245; G01N 27/043; G01N 2001/021; G01N 33/24; G01N 33/245; G01N 33/246
See application file for complete search history.

(56) References Cited

U.S. PATENT DOCUMENTS 3,084,553 A   4/1963   Cullinan et al.
3,224,512 A   12/1965  Alexander
(Continued)

OTHER PUBLICATIONS

Adamchuk et al., "On-the-go soil sensors for precision agriculture", Computers and Electronics in Agriculture, No. 44, pp. 71-91, Jun. 12, 2004.
(Continued)

*Primary Examiner* — Gary S Hartmann
(74) *Attorney, Agent, or Firm* — Jeffrey L. Thompson; Thompson Law, P.A.

(57) ABSTRACT

A system for measuring soil properties on-the-go using a narrow profile sensor unit is provided on an implement for traversing a field. The sensor unit includes a front disk/coulter arranged to open a slot in the soil, a runner assembly arranged to follow behind the front disk/coulter for sliding contact with the soil in the slot, and a rotating disk/spoked wheel arranged to follow behind the runner assembly to close the slot. The front disk or coulter serves as a first electrode of an electrode array, the runner assembly has second and third electrodes attached thereto, and the rotating disk/spoked wheel serves as a fourth electrode. The electrode array can be used to measure soil electrical conductivity at multiple depths and to measure soil moisture. An optical window and pH sensor can also be incorporated into the runner assembly to measure soil reflectance and soil pH.

27 Claims, 14 Drawing Sheets

(51) Int. Cl.
*A01C 21/00* (2006.01)
*A01C 5/06* (2006.01)

(56) References Cited

U.S. PATENT DOCUMENTS

| | | | |
|---|---|---|---|
| 3,331,249 A | | 7/1967 | Boxrud |
| 3,464,504 A | | 9/1969 | Stange |
| 3,593,809 A | | 7/1971 | Derry |
| 3,625,296 A | | 12/1971 | Mabry |
| 3,774,237 A | | 11/1973 | Hardway, Jr. |
| 4,191,263 A | | 3/1980 | Malterer |
| 4,316,393 A | | 2/1982 | Philipenko |
| RE30,901 E | | 4/1982 | Boxrud |
| 4,332,301 A | | 6/1982 | Jonell |
| 4,333,541 A | | 6/1982 | Doty |
| 4,482,021 A | | 11/1984 | Repski |
| 4,531,087 A | | 7/1985 | Larson |
| 4,534,231 A | | 8/1985 | Jonsson et al. |
| 5,021,939 A | | 6/1991 | Pulgiese |
| 5,033,397 A | * | 7/1991 | Colburn, Jr. ......... A01B 79/005 111/118 |
| 5,076,372 A | | 12/1991 | Hellbusch |
| 5,211,248 A | | 5/1993 | Nosewicz et al. |
| 5,394,949 A | | 3/1995 | Wright et al. |
| 5,435,399 A | | 7/1995 | Peterson et al. |
| 5,524,560 A | * | 6/1996 | Carter ................. A01B 63/114 111/200 |
| 5,673,637 A | * | 10/1997 | Colburn, Jr. ......... A01B 79/005 111/118 |
| 5,741,983 A | | 4/1998 | Skotnikov et al. |
| 5,841,282 A | | 11/1998 | Christy et al. |
| 5,887,491 A | | 3/1999 | Monson et al. |
| 5,950,741 A | | 9/1999 | Wright et al. |
| 6,016,713 A | | 1/2000 | Hale |
| 6,116,172 A | | 9/2000 | Prairie et al. |
| 6,138,590 A | * | 10/2000 | Colburn, Jr. ......... A01B 79/005 111/118 |
| 6,237,429 B1 | | 5/2001 | Melnyk |
| 6,260,633 B1 | | 7/2001 | Machek et al. |
| 6,360,829 B1 | | 3/2002 | Naber et al. |
| 6,363,803 B1 | | 4/2002 | Hubers |
| 6,484,652 B1 | * | 11/2002 | Colburn, Jr. ......... A01B 79/005 111/118 |
| 6,592,820 B1 | | 7/2003 | Hardman et al. |
| 6,766,865 B1 | | 7/2004 | Dagel et al. |
| 6,959,245 B2 | | 10/2005 | Rooney et al. |
| 6,975,245 B1 | | 12/2005 | Slater et al. |
| 7,216,555 B2 | | 5/2007 | Drummond et al. |
| 7,255,016 B2 | | 8/2007 | Burton |
| 7,552,654 B2 | | 6/2009 | Burton |
| 7,827,873 B2 | | 11/2010 | Burton |
| 8,204,689 B2 | * | 6/2012 | Christy ................. A01B 79/005 702/28 |
| 8,451,449 B2 | | 5/2013 | Holland |
| 8,573,074 B1 | | 11/2013 | Marker |
| 9,113,589 B2 | * | 8/2015 | Bassett ................. A01C 7/205 |
| 9,285,501 B2 | * | 3/2016 | Christy ................. G01N 21/359 |
| 9,651,536 B1 | * | 5/2017 | Lund ..................... A01C 21/00 |
| 9,743,574 B1 | * | 8/2017 | Maxton ................ A01B 79/005 |
| 2002/0131046 A1 | | 9/2002 | Christy et al. |
| 2003/0016029 A1 | | 1/2003 | Schuler et al. |
| 2004/0052686 A1 | | 3/2004 | Hardman et al. |
| 2005/0034437 A1 | | 2/2005 | McMurtry et al. |
| 2005/0172733 A1 | | 8/2005 | Drummond et al. |
| 2005/0279163 A1 | | 12/2005 | Chesk |
| 2006/0114006 A1 | | 6/2006 | Mohamed |
| 2007/0068238 A1 | | 3/2007 | Wendte |
| 2007/0151467 A1 | | 7/2007 | Furll et al. |
| 2008/0199359 A1 | | 8/2008 | Davis et al. |
| 2009/0112475 A1 | * | 4/2009 | Christy ................. A01B 79/005 702/5 |
| 2010/0275565 A1 | | 11/2010 | Moe et al. |
| 2011/0106451 A1 | | 5/2011 | Christy et al. |
| 2011/0203356 A1 | | 8/2011 | Scherbring |
| 2012/0048160 A1 | | 3/2012 | Adams et al. |
| 2012/0089304 A1 | | 4/2012 | Hamilton et al. |
| 2012/0091222 A1 | | 4/2012 | Dresselhaus et al. |
| 2012/0130552 A1 | | 5/2012 | Schmidt et al. |
| 2013/0046446 A1 | | 2/2013 | Anderson |
| 2013/0191073 A1 | | 7/2013 | Rice et al. |
| 2013/0250305 A1 | | 9/2013 | Holland |
| 2013/0325267 A1 | | 12/2013 | Adams et al. |
| 2014/0116735 A1 | | 5/2014 | Bassett |
| 2014/0303854 A1 | | 10/2014 | Zielke |

OTHER PUBLICATIONS

Fares et al., "Improved Calibration Functions of Three Capacitance Probes for the Measurement of Soil Moisture in Tropical Soils", Sensors, No. 11, pp. 4858-4874, May 3, 2011.
Soil EC/OM Precision Mapping, "Know Your Field, Grow Your Field," Veris Technologies, brochure, Salina, Kansas, Feb. 2011.
OpticMapper, Operating Instructions, Veris Technologies, operating instructions/manual, Salina, Kansas, Sep. 2010.

* cited by examiner

SYSTEM FOR MEASURING MULTIPLE SOIL PROPERTIES USING NARROW PROFILE SENSOR CONFIGURATION

RELATED APPLICATIONS

This application claims the benefit of U.S. Provisional Patent Application No. 62/216,087 filed on Sep. 9, 2015. This application also relates to the subject matter of pending U.S. patent application Ser. Nos. 14/253,304 and 14/253,839, both of which were filed on Apr. 15, 2014, and U.S. Provisional Patent Application No. 61/812,131 filed on Apr. 15, 2013. The entire contents of these related applications are incorporated herein by reference.

BACKGROUND OF THE INVENTION

Field of the Invention

The present invention relates generally to methods and systems for measuring and mapping soil properties across a field, and more particularly to a system for measuring soil properties on-the-go using a narrow profile sensor configuration.

Description of the Related Art

Soil texture and organic matter are major factors driving crop productivity. Prior art devices exist to measure these properties using electrical conductivity and optical sensing. However, previously developed devices are bulky and require mounting on a stand-alone implement frame. Pulling those devices requires a unique, separate pass through the field for data collection. The extra pass through the field is an added cost, and the seasonal window to make the measurements is narrow.

Soil moisture is another major factor driving crop productivity, particularly in arid regions. Soil moisture varies spatially within fields due to soil texture, topography, crop usage, irrigation patterns, and various other variables.

Fixed, semi-permanent moisture sensors (e.g., gypsum blocks and neutron probes) and manually inserted sensors (e.g., TDR, capacitance) have been used for many years to monitor soil moisture levels in agricultural fields. However, these moisture sensors do not capture the spatial variability as their expense and manual deployment make it unfeasible to collect enough measurements to produce a spatially accurate map of soil moisture.

Variable rate irrigation allows limited irrigation water supplies to be applied at different rates in different areas of a field. For example, variable rate irrigation can be used to apply more irrigation water to zones of a field where water holding capacity is lower or where crop use or productivity is expected to be greater. Fixed moisture sensors are often used in fields with variable rate irrigation. However, the use of fixed moisture sensors does not link soil moisture with soil properties that affect water-holding capacity and crop usage of water.

Soil pH and other chemical properties are also important factors for crop productivity. Mapping soil pH and other chemical properties is typically done with laboriously collected lab samples, or with a tractor-drawn implement, such as the Veris on-the-go system (pH). However, it is not feasible to map soil pH or other chemical properties at a high density using conventionally collected lab samples, and the cost of a Veris on-the-go system for such mapping measurements is sometimes too expensive.

There is a need for a method and system for on-the-go measurement of multiple soil properties using a narrow profile sensor configuration.

SUMMARY OF THE INVENTION

An object of the present invention is to provide a method and system for on-the-go measurement of soil properties that has a reduced overall size and number of ground-engaging components.

A further object of the present invention is to provide a method and system for on-the-go measurement of soil properties that has ground-engaging components arranged in-line to reduce the draft requirement and the overall size of the implement.

A further object of the present invention is to provide a system for on-the-go measurement of soil properties that can be mounted on an existing implement, such as a planter or fertilizer applicator, or on a light-duty pulling vehicle, such as an ATV.

A further object of the present invention is to provide a method and system for on-the-go measurement of soil properties that allows a dense mapping of multiple soil properties with a relatively low total investment.

A further object of the present invention is to provide a narrow profile sensor unit that can collect soil electrical conductivity, soil optical, and soil moisture simultaneously.

A further object of the present invention is to provide a soil pH sensing unit mounted to a soil engaging runner for collecting soil pH measurements in situ.

To accomplish these and other objects of the invention, a method and system are provided for measuring multiple soil properties on-the-go using a narrow profile sensor configuration on an implement for traversing a field. The sensor configuration includes a front disk or coulter arranged to open a slot in the soil, a runner arranged to follow behind the front disk or coulter for sliding contact with the soil in the slot, and a rotating disk or a spoked wheel arranged to follow behind the runner to close the slot. The sensor configuration provides an electrode array with the front disk or coulter serving as a first electrode. Second and third electrodes are embedded in a bottom surface of the runner. The rotating disk or spoked wheel following behind the runner serves as a fourth electrode. The electrode array can be used to measure soil electrical conductivity at multiple depths and to measure soil moisture. An optical window and pH sensor can also be incorporated into the runner to measure soil reflectance and soil pH.

According to one aspect of the present invention, a system for measuring at least one property of soil in a field is provided, comprising: a first soil engaging component arranged to open a slot in the soil, the first soil engaging component comprising a first electrode of an electrode array for measuring soil electrical conductivity; a second soil engaging component comprising a runner arranged to follow behind the first soil engaging component to contact soil in the slot, the runner comprising second and third electrodes of the electrode array; and a third soil engaging component arranged to follow behind the second soil engaging component to contact soil in or adjacent to the slot, the third soil engaging component comprising a fourth electrode of the electrode array.

According to another aspect of the present invention, a system for measuring pH of soil in a field is provided, comprising: a narrow profile runner arranged to open a slot in the soil; and a pH sensor attached to the runner, the pH sensor comprising a pair of ion-selective electrodes and a means for lowering the electrodes into contact with the soil in the slot to measure pH of the soil.

According to another aspect of the present invention, a row crop implement is provided, comprising: a plurality of row units for tilling, fertilizing or planting a plurality of parallel rows in soil, the plurality of row units comprising two adjacent row units; and a narrow profile sensor unit arranged between the two adjacent row units. The sensor unit comprises a front disk or coulter arranged to open a slot in the soil, a runner arranged to follow behind the front disk or coulter for sliding contact with the soil in the slot, and a rotating disk or a spoked wheel arranged to follow behind the runner to close the slot.

Numerous other objects of the present invention will be apparent to those skilled in this art from the following description wherein there is shown and described embodiments of the present invention, simply by way of illustration of some of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

A method and system for measuring multiple soil properties according to the present invention will now be described in detail with reference to FIGS. 1 to 13 of the accompanying drawings.

Figure 1:
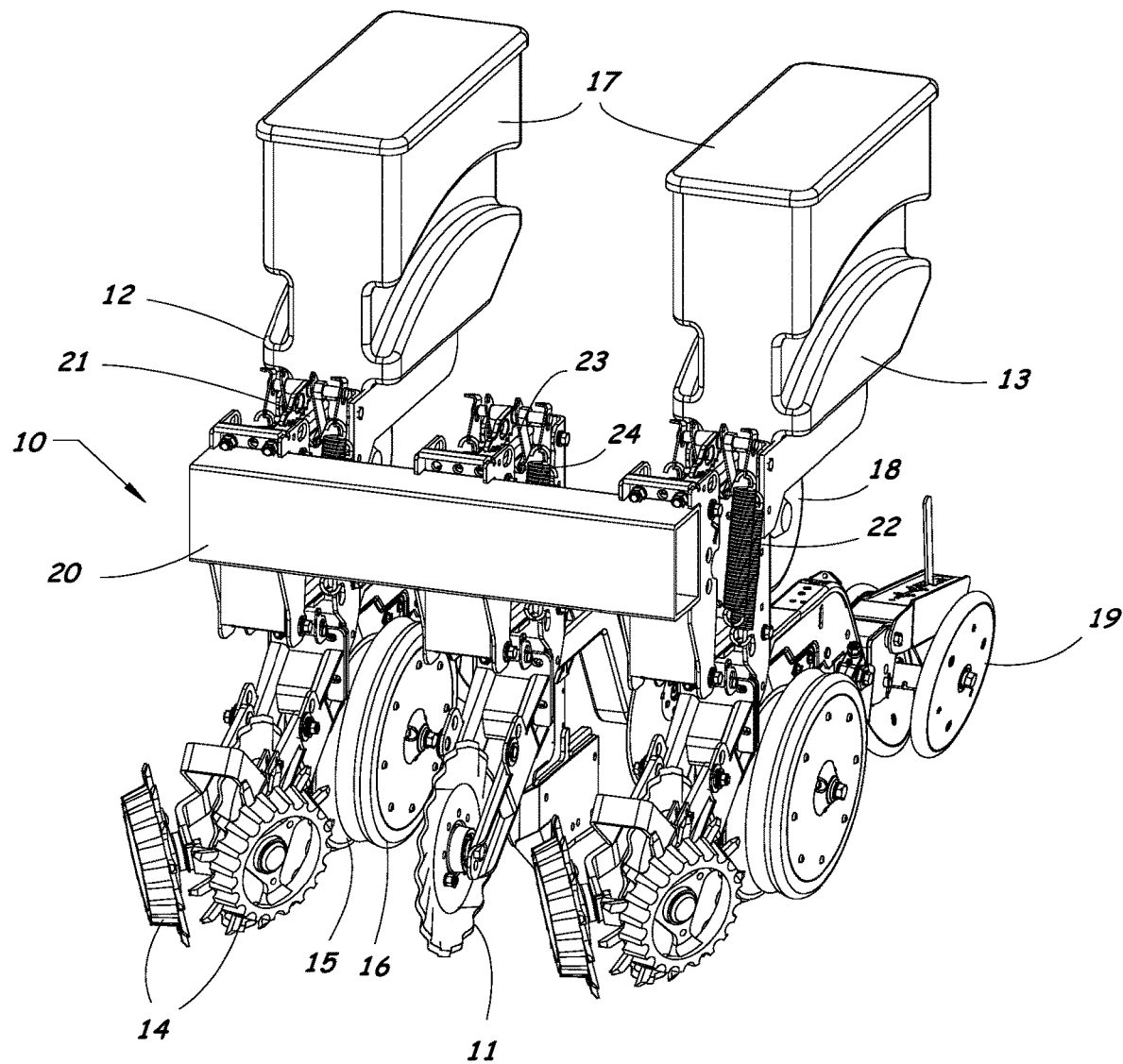
FIG. 1 is a front perspective view of a row crop implement equipped with a narrow profile sensor unit positioned between two adjacent row units.
Figure 2:
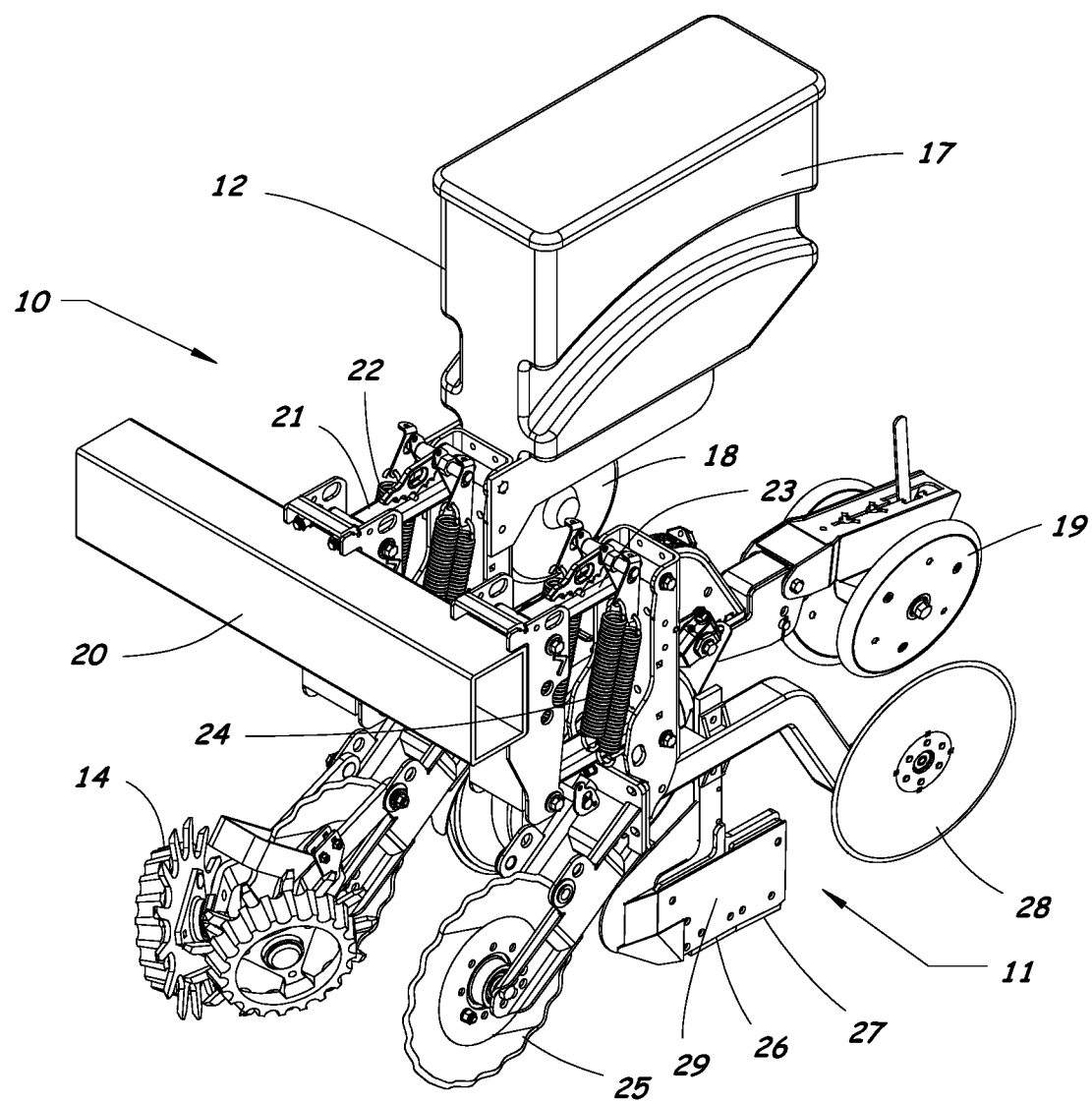
FIG. 2 is another front perspective view of the row crop implement with one of the row units removed to illustrate the narrow profile sensor unit of the present invention.
Figure 3:
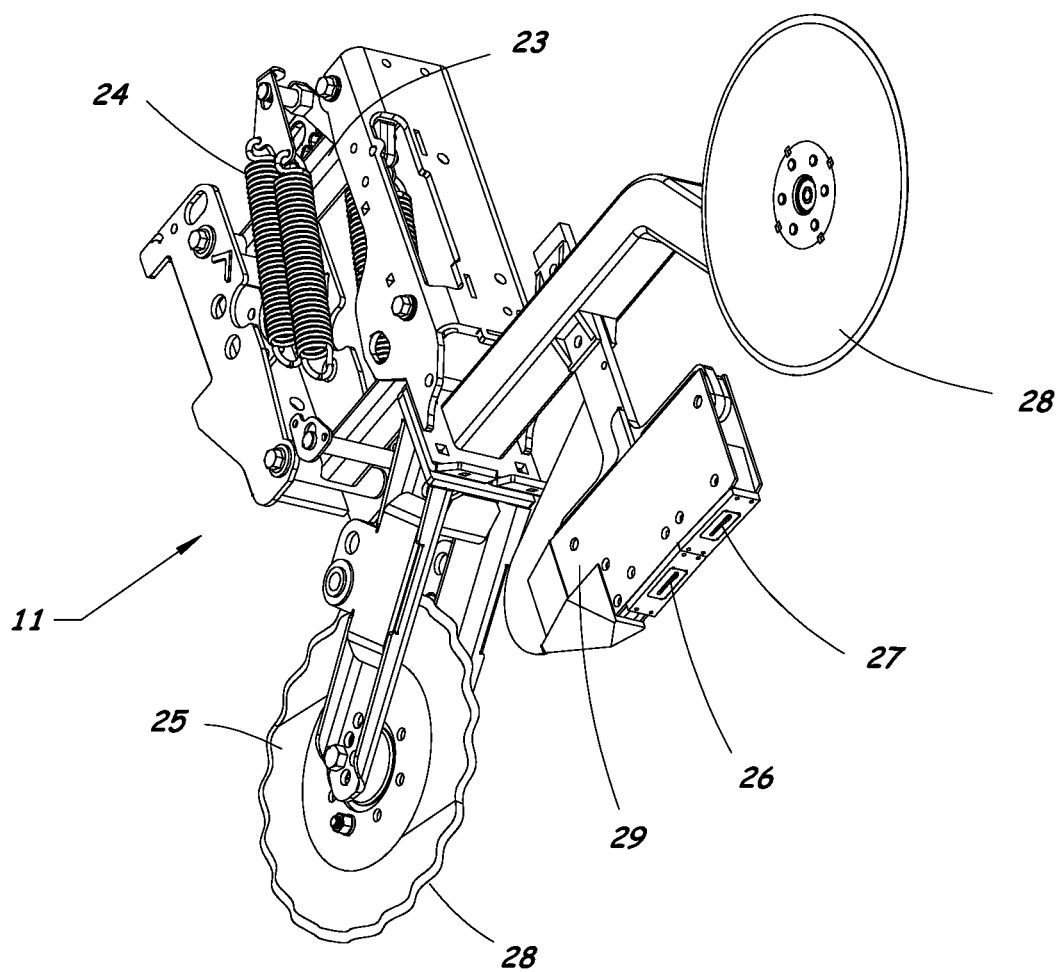
FIG. 3 is a lower left side perspective view of the narrow profile sensor unit according to a first embodiment of the present invention.
Figure 4:
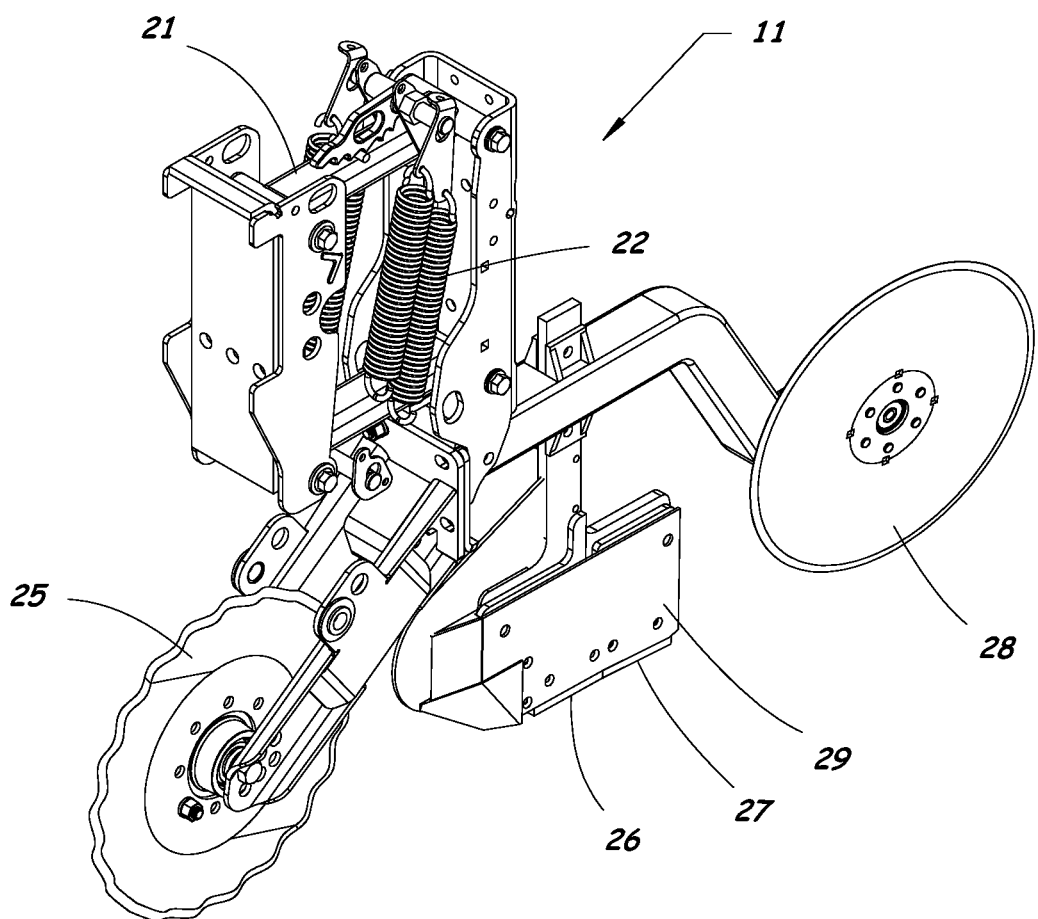
FIG. 4 is a front perspective view of the narrow profile sensor unit shown in FIG. 3.
Figure 5:
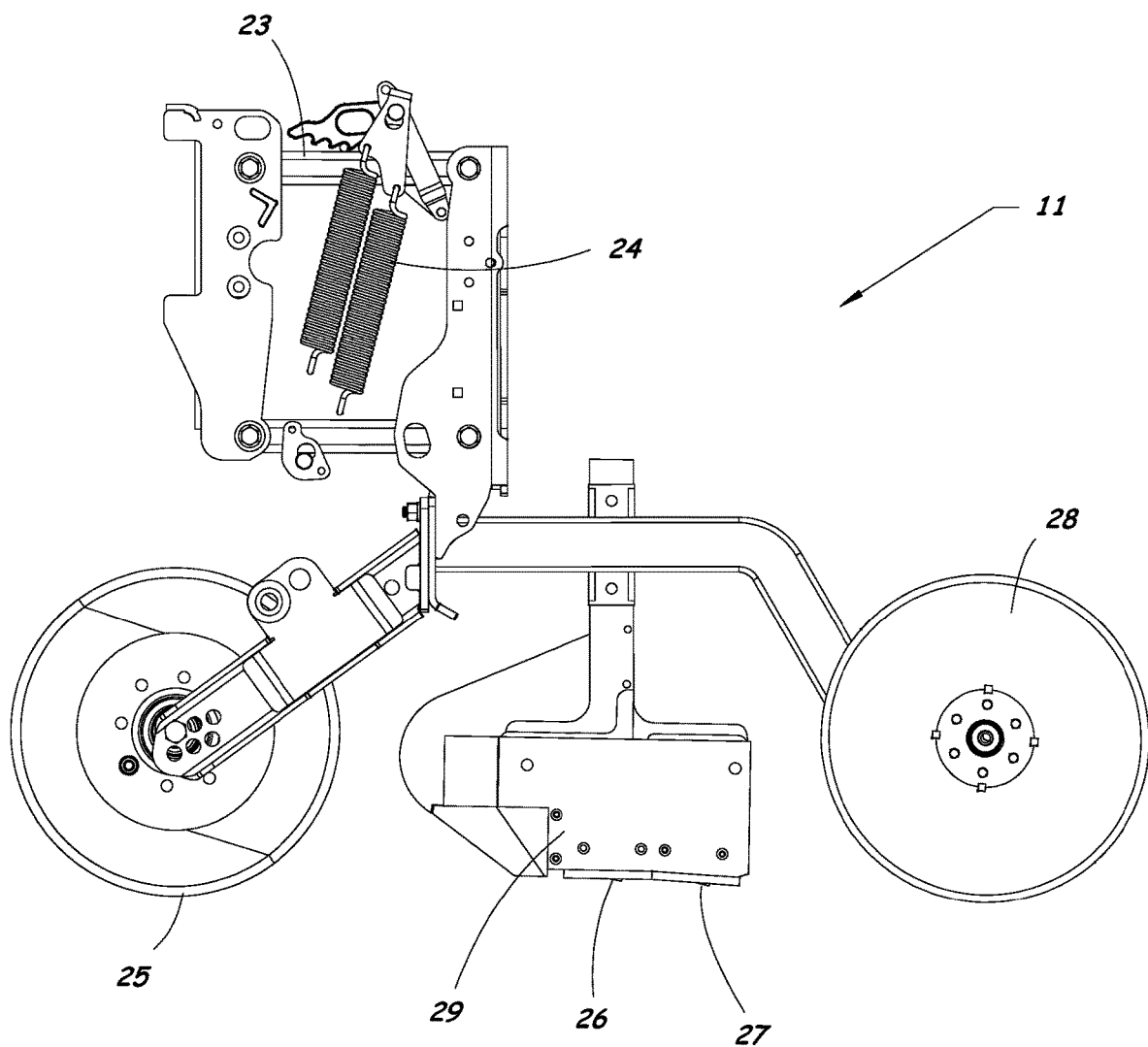
FIG. 5 is a side elevation view of the narrow profile sensor unit shown in FIG. 3.

FIGS. 1 and 2 illustrate a row crop implement 10 equipped with a narrow profile sensor unit 11 according to the present invention. The narrow profile sensor unit 11 is positioned between two adjacent row units 12, 13 of the implement 10. The row units 12, 13 can be planter row units, as shown in FIGS. 1 and 2. Alternatively, the row units can be conventional strip tillage units or fertilizer applicator row units, which are attached to an implement tool bar.

The planter row units 12, 13 each have a row clearing assembly 14 for moving crop residue and debris to the sides of the row, a furrow opener assembly 15 with gauge wheels 16 for opening a furrow in the soil, a seed hopper 17, a seed metering mechanism 18 for dropping seeds through a seed tube into the furrow, and a furrow closing assembly 19. The row units 12, 13 are attached to a planter tool bar 20 by parallel linkage assemblies 21. Springs 22 are attached to the parallel linkage assemblies 21 to transfer additional down pressure from the toolbar 20 to the row units 12, 13.

The narrow profile sensor unit 11 is attached to the same tool bar 20 as the conventional row units 12, 13 using a similar parallel linkage assembly 23 and springs 24 for transferring additional down pressure from the toolbar 20 to the sensor unit 11. This allows the implement 10 to be used for its original purpose of planting, tilling or fertilizing, as well as for measuring various properties of the soil in the field. The soil property measurements using the narrow profile sensor unit 11 can thus be made in conjunction with a farming pass already being made in the field.

Alternatively, the narrow profile sensor unit 11 can be installed on a light-duty frame for pulling with an ATV-type vehicle in a separate pass over the field. Conventional systems for measuring soil conductivity typically have each electrode of a four electrode array cutting its own path in the soil. The in-line design of the narrow profile sensor unit 11 of the present invention results in a lower draft requirement as compared to such conventional systems.

The narrow profile sensor unit 11 includes a first soil engaging component 25, a second soil engaging component 26, a third soil engaging component 27, and a fourth soil engaging component 28. The first, second, third and fourth soil engaging components 25, 26, 27, 28 are arranged substantially in-line with each other so that the second, third and fourth soil engaging components 26, 27, 28 follow directly behind the first soil engaging component 25 during forward movement of the implement through the field. By using soil engaging components 25-28 that are substantially aligned with each other in a direction of travel, the draft requirement for the sensor unit 11 is reduced and the sensor unit 11 can be made more compact.

The first soil engaging component 25 is a rotating disk or coulter arranged to open a slot in the soil. The second and third soil engaging components 26, 27 are attached to the bottom of a runner 29 arranged to follow behind the first soil engaging component 25 for sliding contact with the soil in the slot created by the first soil engaging component 25. The fourth soil engaging component 28 is a rotating disk or spoked wheel arranged to follow behind the runner 26 to close the slot.

In the embodiment shown in FIGS. 1 to 5, the first, second, third and fourth soil engaging components 25-28 of the narrow profile sensor unit 11 provide a four electrode array for measuring soil electrical conductivity. The electrode array includes the first soil engaging component 25 functioning as the first electrode for contacting the soil. The second and third soil engaging components 26, 27 attached to the bottom of the runner 29 function as the second and third electrodes of the electrode array. The second and third soil engaging components 26, 27 each have an angled leading edge that projects below the bottom surface of the runner 29 and slopes downwardly and rearwardly to provide better soil contact. The fourth soil engaging component 28 functions as the fourth electrode of the electrode array.

The electrode array can be a Wenner or Schlumberger array with the first and fourth electrodes 25, 28 connected to a source of electrical current to inject electrical current into the soil, and the second and third electrodes 26, 27 connected to a voltage measuring circuit to measure the voltage drop in the injected electrical current from the first and fourth electrodes 25, 28.

Figure 6:
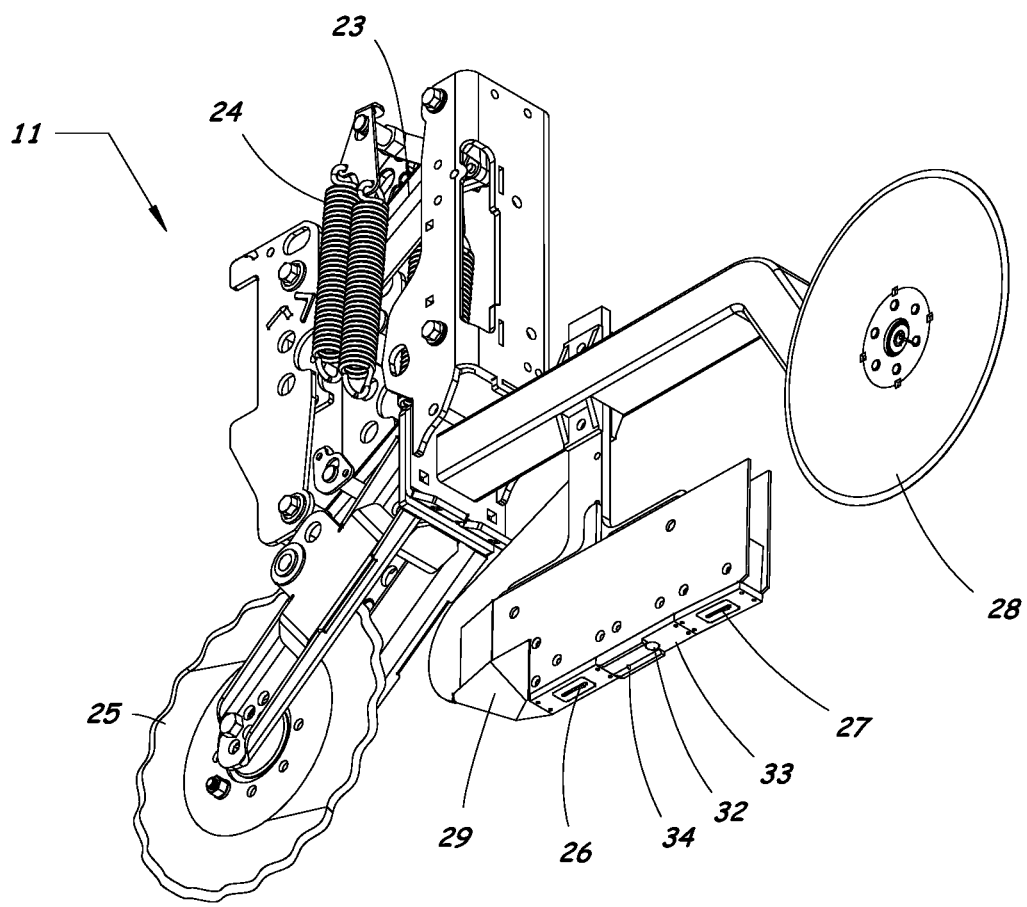
FIG. 6 is a lower left side perspective view of a narrow profile sensor unit with an optical window positioned in the lower surface of the runner between two embedded electrodes according to a second embodiment of the present invention.

The narrow profile sensor unit 11 can be equipped with other sensors for measuring soil properties. As shown in FIG. 6, the runner 29 can be made with an optical window 32 in the lower soil engaging surface 33 between the second and third electrodes 26, 27. A sensor for measuring optical reflectance of the soil through the optical window 32 is contained within the runner 29. A pair of protective fins 34 are positioned on right and left sides of the optical window 32 and protrude from the runner 29 below a lower surface of the optical window 32 for protecting the window 32 during use.

Figure 7:
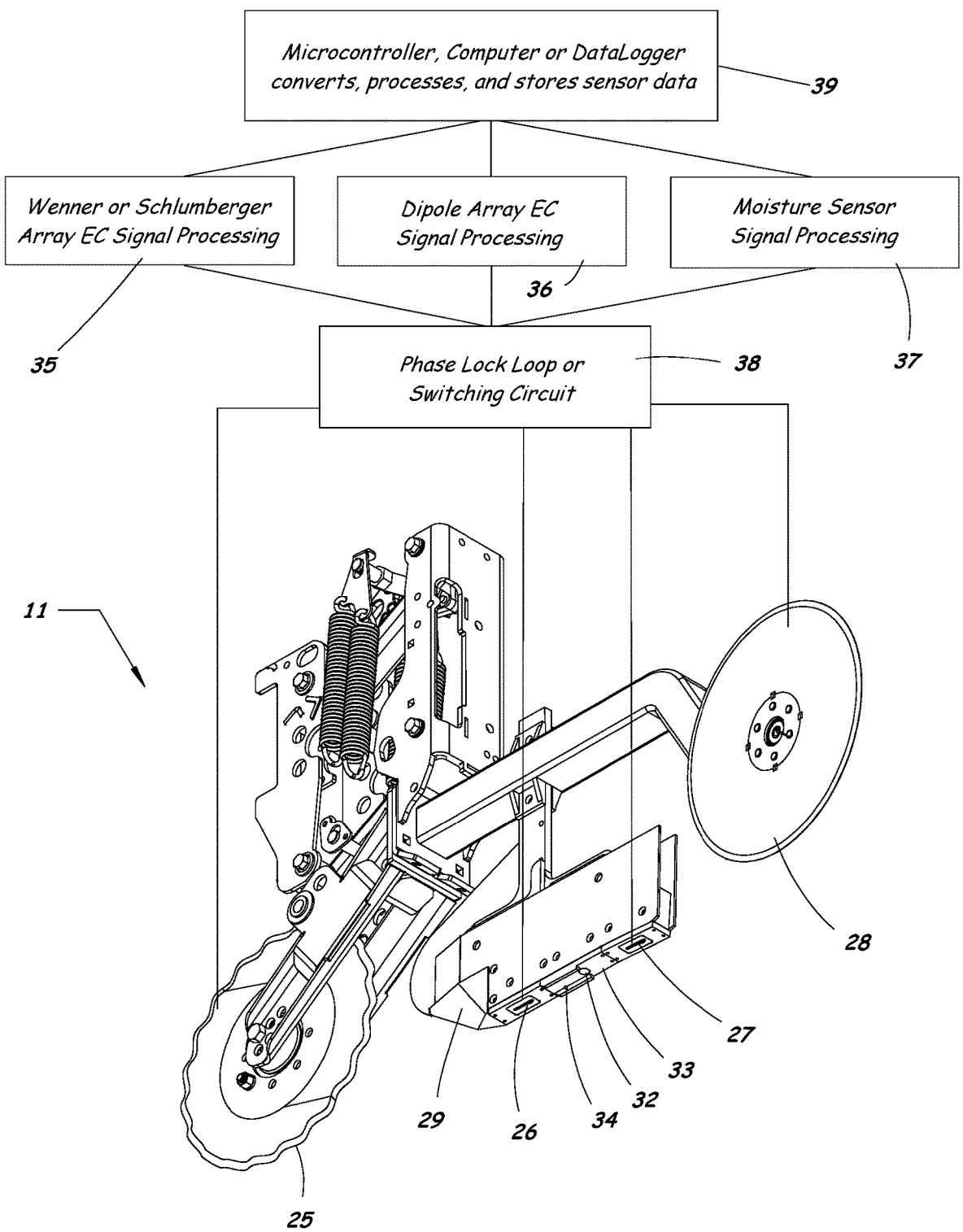
FIG. 7 is a lower left side perspective view of the narrow profile sensor unit shown in FIG. 6, with a diagram illustrating the various signal processing circuits that can be used with the sensor unit to detect multiple soil properties.

As shown in FIG. 7, the narrow profile sensor unit 11 can be equipped with multiple signal processing circuits to measure a plurality of soil properties using the same soil engaging components 25-28. A first signal processing circuit 35 is provided for using the electrode array 25-28 as a Wenner or Schlumberger array for measuring soil electrical conductivity at a relatively deep depth (e.g., 1 to 3 feet). A second signal processing circuit 36 is provided for using the electrode array as a dipole array for measuring soil electrical conductivity at a relatively shallow depth (e.g., less than 12 inches). A third signal processing circuit 37 (e.g., a capacitance circuit) is provided for using two electrodes 26, 27 of the electrode array to measure and generate a soil moisture signal.

A phase lock loop or a switching circuit 38 is provided between the electrodes 25-28 and the first, second and third signal processing circuits 35-37 to allow the signal processing circuits 35-37 to measure soil electrical conductivity at both the deep and shallow depths, as well as soil moisture, using the same electrode array 25-28. For example, the phase lock loop can be used to differentiate the four electrode array signal from the dipole signal, or the switching circuit can be used to rapidly switch between the signal processing circuits 35-37. The signal processing circuits 35-37 are connected to a micro controller, computer or data logger 39 to convert, process and store the sensor data received from the signal processing circuits 35-37.

Figure 8:
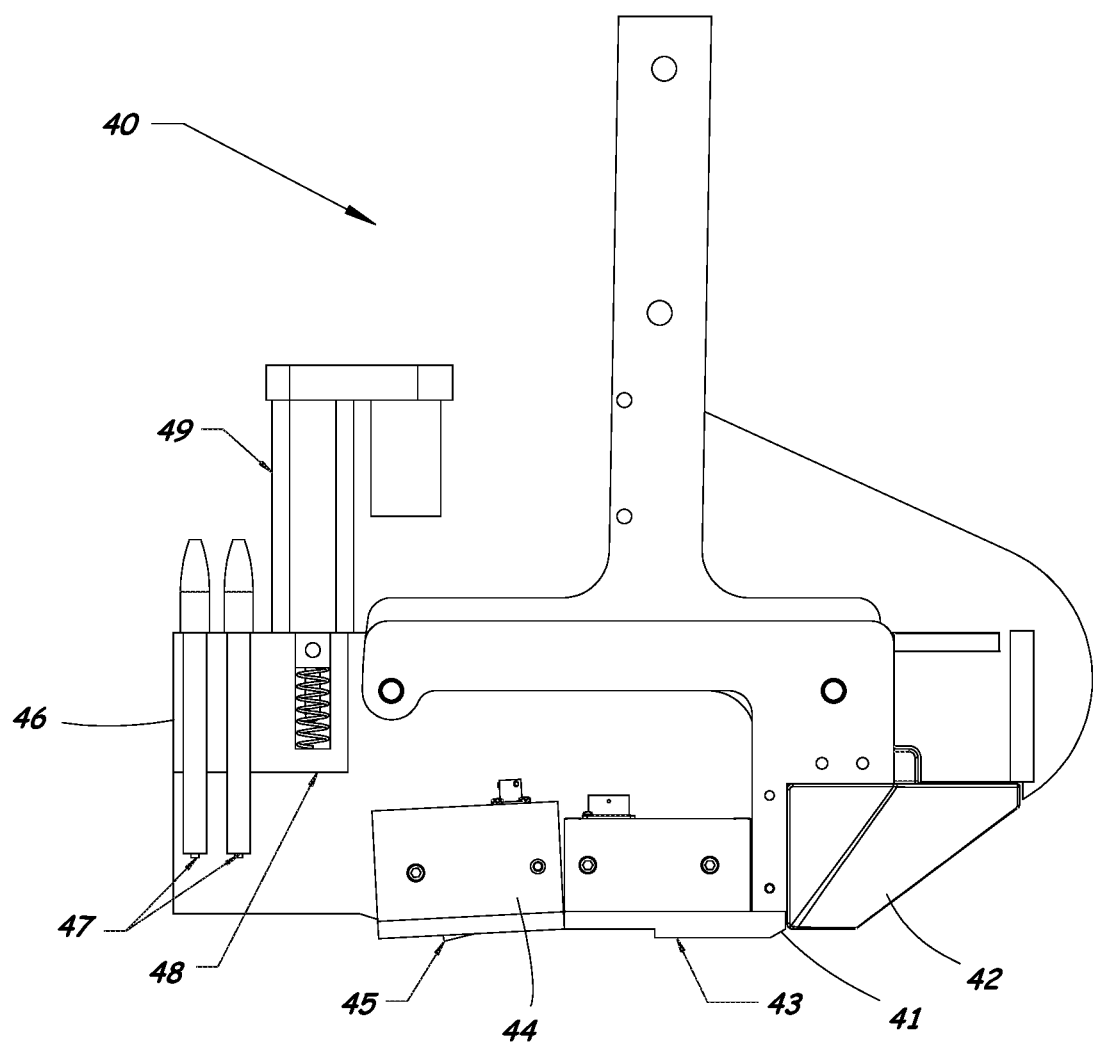
FIG. 8 is an elevation view of a runner having a pH sensor located behind the optical sensor and conductivity sensor for sensing soil pH according to a third embodiment of the present invention.
Figure 9:
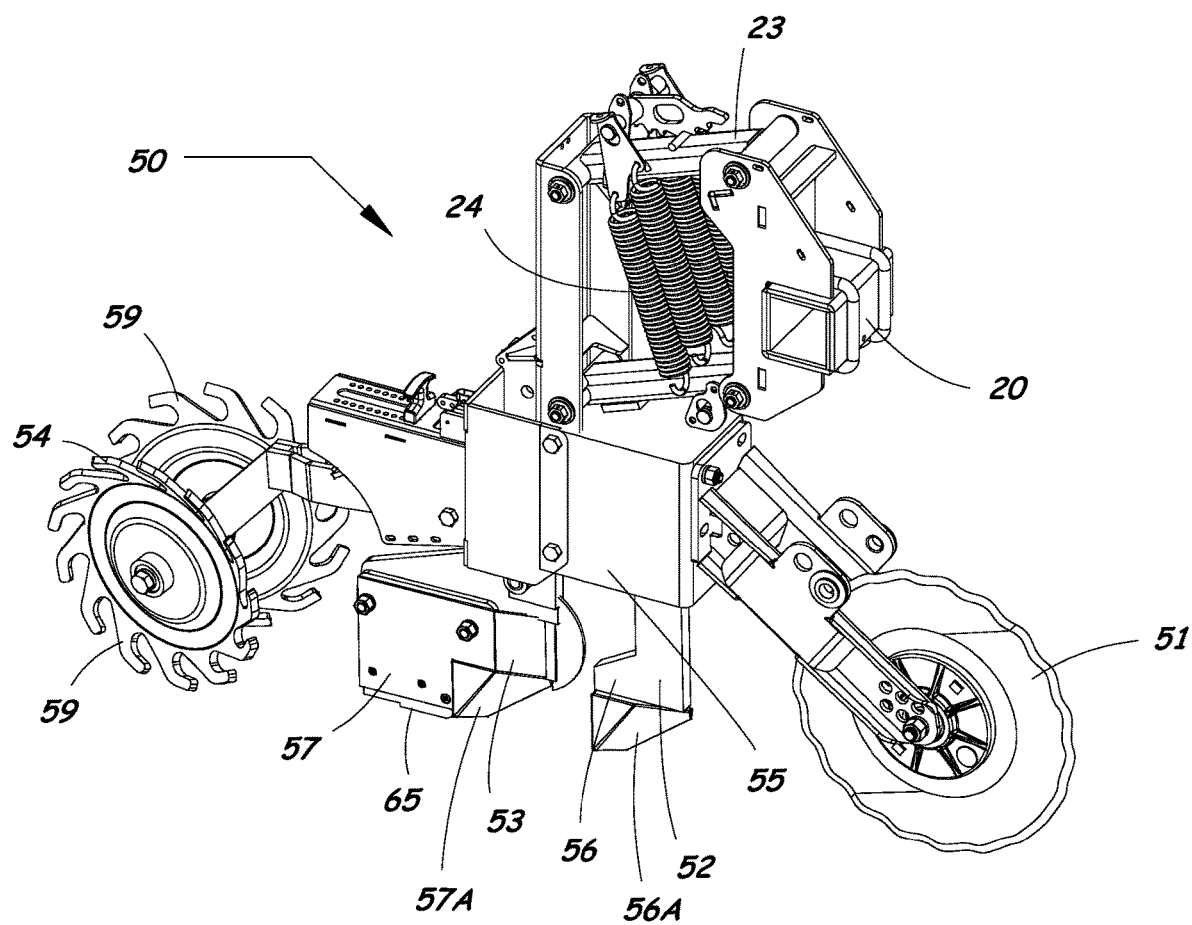
FIG. 9 is a front perspective view of a narrow profile sensor unit according to another embodiment of the present invention.
Figure 10:
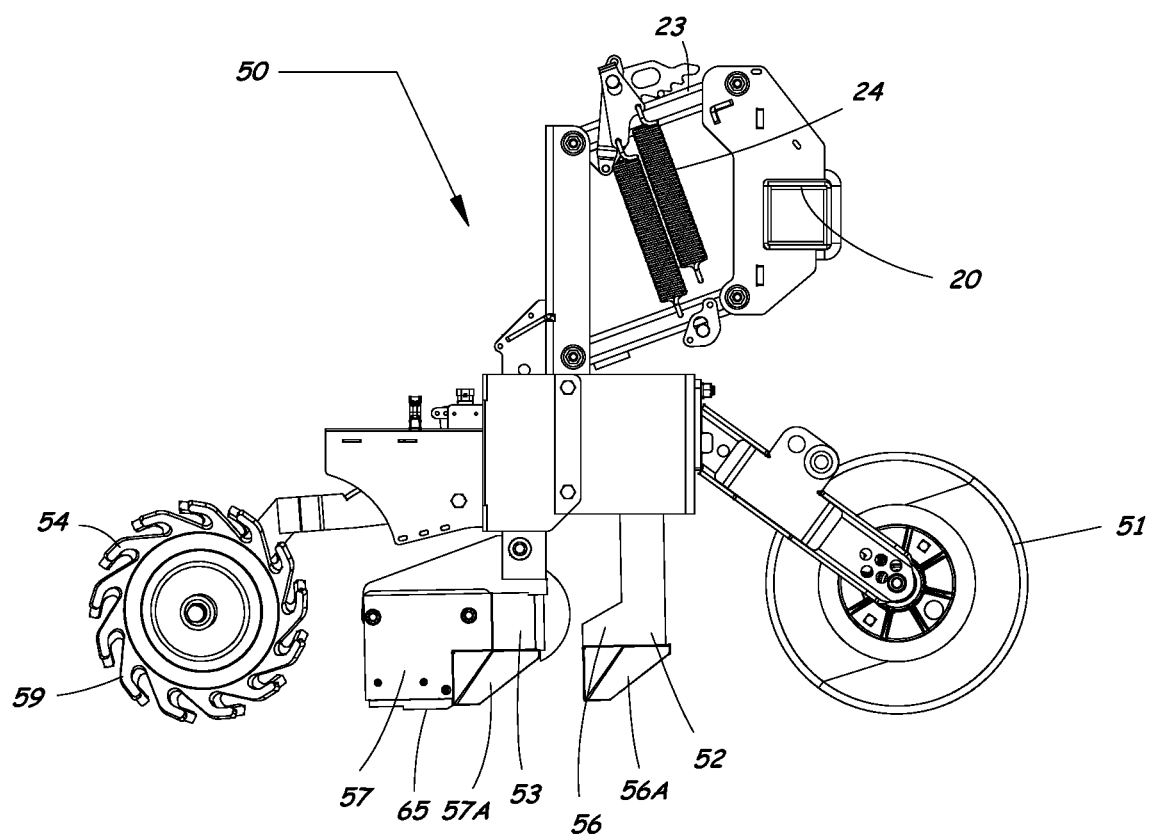
FIG. 10 is a side elevation view of the narrow profile sensor unit shown in FIG. 9.
Figure 11:
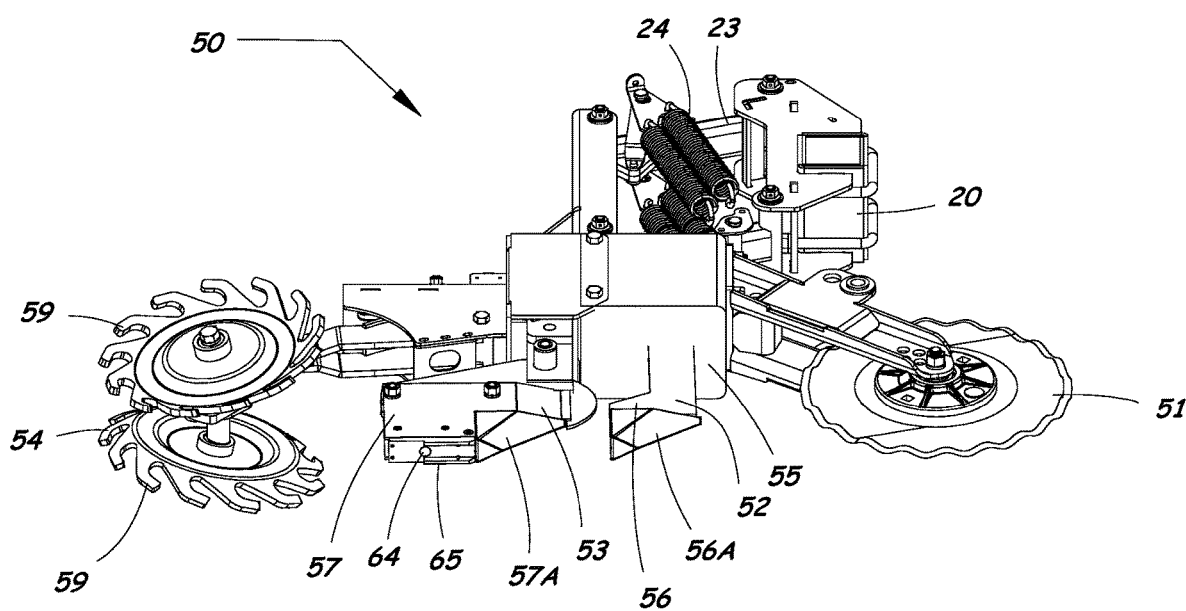
FIG. 11 is a lower right side perspective view of the narrow profile sensor unit shown in FIG. 9.
Figure 12:
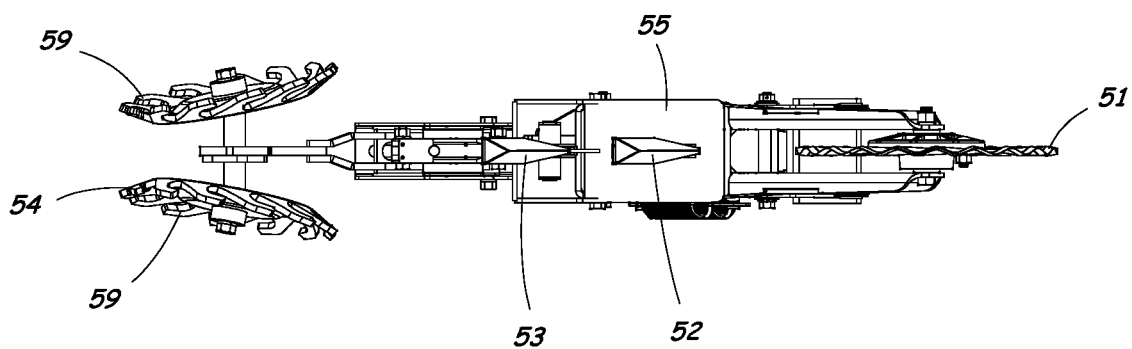
FIG. 12 is a bottom view of the narrow profile sensor unit shown in FIG. 9.
Figure 14:
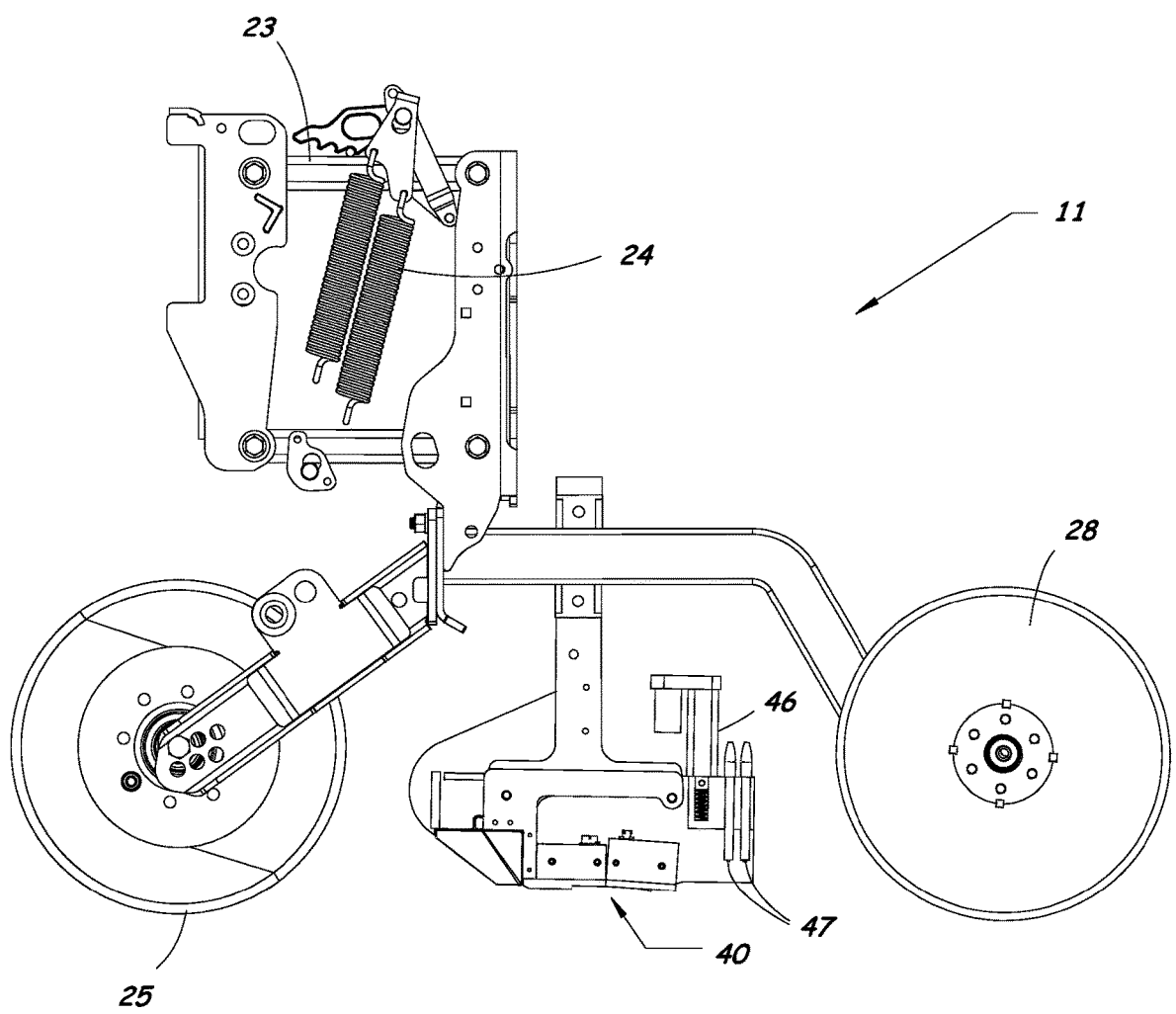
FIG. 14 is a side elevation view of a narrow profile sensor unit with a runner having a pH sensor.

FIGS. 8 and 14 show a system for measuring pH of soil in a field incorporated into a runner 40 suitable for use in the narrow profile sensor unit 11. A front portion 41 of the runner 40 includes leading edge 42, an optical sensor module 43 with an optical window positioned in a bottom surface of the runner 40, and a conductivity sensor module 44 with one or more electrodes 45 positioned behind the optical sensor module 43 for sliding contact with the soil in the slot. The electrode 45 has an angled leading edge that slopes downwardly and rearwardly to provide better soil contact.

A pH sensor 46 having at least one ion selective electrode 47 is attached to a rear portion of the runner 40 behind the conductivity sensor module 44. The pH sensor 46 in the illustrated embodiment includes a pair of ion-selective electrodes 47, an electrode holder 48, and a linear actuator 49 for lowering the electrodes 47 into contact with the soil in the bottom of the slot opened by the front portion 41 of the runner 40.

In use, the pH sensor 46 can be lowered into contact with the soil in the bottom of the slot when the implement is stopped. The pH sensor 46 collects a pH measurement of the soil in situ. The runner 40 can also be used to collect soil reflectance data using the optical sensor module 43, and to collect soil electrical conductivity data or soil moisture data using the conductivity sensor module 44. The soil reflectance measurements and soil electrical conductivity measurements are collected on-the-go while the implement is traversing the field, while the pH measurements are collected when the implement is stopped at predetermined locations in the field.

FIGS. 9 to 12 show a narrow profile sensor unit 50 according to another embodiment of the invention. The narrow profile sensor unit 50 includes a first soil engaging component 51, a second soil engaging component 52, a third soil engaging component 53, and a fourth soil engaging component 54. The first, second, third and fourth soil engaging components 51, 52, 53, 54 are arranged substantially in-line with each other so that the second, third and fourth soil engaging components 52, 53, 54 follow behind the first soil engaging component 51 during forward movement of the implement through the field. The narrow profile sensor unit 50 is substantially the same as the narrow profile sensor unit 11 of the embodiment described above, except that the second, third and fourth soil engaging components 52, 53, 54 are different.

The first soil engaging component 51 shown in FIGS. 9 to 12 is a rotating coulter 51 arranged to open a slot in the soil. The second and third soil engaging components 52, 53 are part of a runner assembly 55 having a leading shank 56 and a runner 57 arranged to follow behind the leading shank 56. The leading shank 56 has a replaceable soil engaging wear plate 56A and is arranged to follow behind the first soil engaging component 51 for sliding contact with the soil in the slot created by the first soil engaging component 51. The runner 57 has a replaceable soil engaging wear plate 57A and is arranged to follow behind the leading shank 56 for sliding contact with the soil in the slot behind the leading shank 56. The wear plates 56A, 57A can be made of a material having a high wear resistance, such as chromium carbide.

The fourth soil engaging component 54 in the illustrated embodiment is a pair of spoked wheels 59 arranged to follow behind the runner 57 to close the slot.

In the embodiment shown in FIGS. 9 to 12, the first, second, third and fourth soil engaging components 51, 52, 53, 54 of the narrow profile sensor unit 50 provide a four electrode array for measuring soil electrical conductivity. The electrode array includes the first soil engaging component 51 functioning as the first electrode for contacting the soil. Second and third electrodes of the electrode array are the leading shank 56 and the runner 57 and their respective wear plates 56A, 57A. One of the spoked wheels 59 of the fourth soil engaging component 54 functions as the fourth electrode of the electrode array. Various signal processing circuits can be used with the electrode array, similar to the first embodiment described above.

The narrow profile sensor unit 50 is also equipped with other sensors for measuring soil properties. The runner 57 includes an optical window 64 in the lower soil engaging surface. A sensor for measuring optical reflectance of the soil through the optical window 64 is contained within the runner 57. A pair of protective fins 65 are positioned on right and left sides of the optical window 64 and protrude from the runner 57 below a lower surface of the optical window 64 for protecting the window 64 during use.

Figure 13:
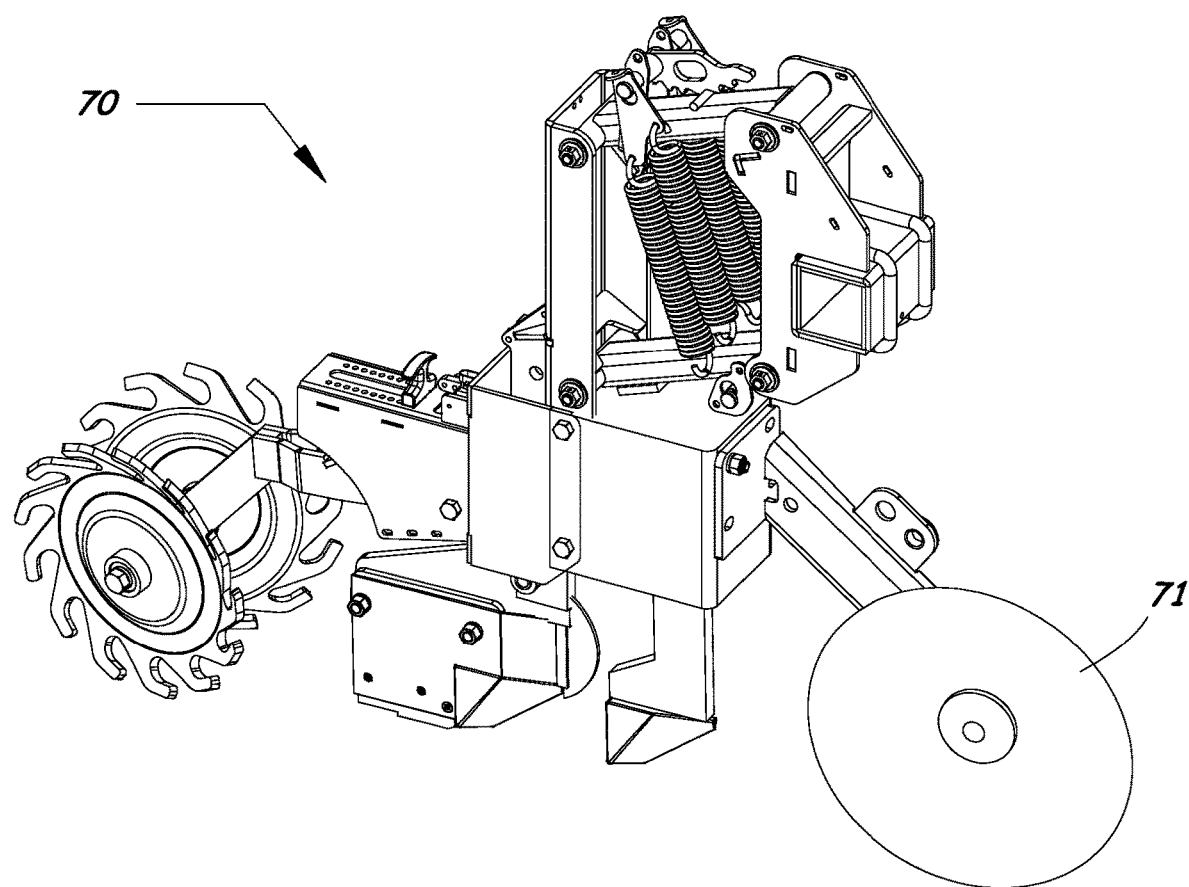
FIG. 13 is a front perspective view of a narrow profile sensor unit according to another embodiment of the present invention.

FIG. 13 illustrates a narrow profile sensor unit 70, which is substantially the same as the unit 50 shown in FIGS. 9 to 12, except that the first soil engaging component is a rotating disk 71 instead of a coulter.

While the invention has been described in connection with specific embodiments thereof, it is to be understood that this is by way of illustration and not of limitation, and the scope of the appended claims should be construed as broadly as the prior art will permit.

What is claimed is:

1. A system for measuring at least one property of soil in a field, comprising:
    a first soil engaging component arranged to open a slot in the soil, said first soil engaging component comprising a rotating disk or coulter that serves as a first electrode of an electrode array for measuring soil electrical conductivity;
    a second soil engaging component comprising a second electrode of said electrode array arranged to follow behind said first soil engaging component to contact soil in said slot;
    a third soil engaging component comprising a third electrode of said electrode array arranged to follow behind said second soil engaging component to contact soil in said slot; and
    a fourth soil engaging component comprising a rotating disk or a spoked wheel arranged to follow behind said third soil engaging component to close said slot, said fourth soil engaging component comprising a fourth electrode of said electrode array.

2. The system according to claim 1, wherein said second and third electrodes are attached to a runner assembly and arranged for sliding contact with the soil in said slot.

3. The system according to claim 1, wherein said electrode array is a Wenner or Schlumberger array with said first and fourth electrodes connected to a source of electrical current and said second and third electrodes connected to a voltage measuring circuit.

4. The system according to claim 1, further comprising a first signal processing circuit for using said electrode array as a Wenner or Schlumberger array for measuring soil electrical conductivity at a first depth, and a second signal processing circuit for using said electrode array as a dipole array for measuring soil electrical conductivity at a second depth, said first depth being deeper than said second depth.

5. The system according to claim 4, further comprising a phase lock loop or switching circuit associated with said first and second signal processing circuits to allow said signal processing circuits to simultaneously measure soil electrical conductivity at said first and second depths using said electrode array.

6. The system according to claim 5, further comprising a micro controller, computer or data logger for converting, processing and storing sensor data received from said signal processing circuits.

7. The system according to claim 1, further comprising a soil moisture signal processing circuit connected to said electrode array for using at least one of said electrodes to measure soil moisture.

8. The system according to claim 7, wherein said soil moisture signal processing circuit comprises a capacitance circuit for generating a soil moisture signal.

9. The system according to claim 7, further comprising a soil electrical conductivity signal processing circuit for using said electrical array for measuring soil electrical conductivity, and a phase lock loop or switching circuit associated with said soil electrical conductivity signal processing circuit and said soil moisture signal processing circuit to allow said signal processing circuits to measure both soil electrical conductivity and soil moisture using said electrode array.

10. The system according to claim 9, further comprising a micro controller, computer or data logger for converting, processing and storing sensor data received from said signal processing circuits.

11. The system according to claim 2, further comprising a pH sensor attached to said runner assembly, said pH sensor comprising at least one electrode arranged to be lowered into contact with the soil in the slot to measure soil pH.

12. The system according to claim 3, wherein said second and third electrodes are attached to a runner assembly and arranged for sliding contact with the soil in said slot.

13. The system according to claim 1, further comprising an optical window located inline with said soil engaging components, and a sensor for measuring optical reflectance of the soil through said window.

14. The system according to claim 12, further comprising a first signal processing circuit for using said electrode array as a Wenner or Schlumberger array for measuring soil electrical conductivity at a first depth, and a second signal processing circuit for using said electrode array as a dipole array for measuring soil electrical conductivity at a second depth, said first depth being deeper than said second depth.

15. The system according to claim 14, further comprising a phase lock loop or switching circuit associated with said first and second signal processing circuits to allow said signal processing circuits to simultaneously measure soil electrical conductivity at said first and second depths using said electrode array.

16. The system according to claim 15, further comprising a micro controller, computer or data logger for converting, processing and storing sensor data received from said signal processing circuits.

17. The system according to claim 16, further comprising a third signal processing circuit connected to said electrode array for using at least one of said electrodes to measure soil moisture.

18. The system according to claim 17, wherein said third signal processing circuit comprises a capacitance circuit for generating a soil moisture signal.

19. The system according to claim 1, further comprising a soil electrical conductivity signal processing circuit for using said electrical array for measuring soil electrical conductivity, a soil moisture signal processing circuit connected to said electrode array for using at least one of said electrodes to measure soil moisture, and a phase lock loop or switching circuit associated with said soil electrical conductivity signal processing circuit and said soil moisture signal processing circuit to allow said signal processing circuits to measure both soil electrical conductivity and soil moisture using said electrode array.

20. The system according to claim 12, further comprising a pH sensor attached to said runner assembly, said pH sensor comprising at least one electrode arranged to be lowered into contact with the soil in the slot to measure soil pH.

21. A system for measuring at least one property of soil in a field, comprising:
- a first soil engaging component arranged to open a slot in the soil, said first soil engaging component comprising a first electrode of an electrode array for measuring soil electrical conductivity;
- a second soil engaging component comprising a second electrode of said electrode array arranged to follow behind said first soil engaging component to contact soil in said slot;
- a third soil engaging component comprising a third electrode of said electrode array arranged to follow behind said second soil engaging component to contact soil in said slot;
- a fourth soil engaging component arranged to follow behind said third soil engaging component to contact soil in or adjacent to said slot, said fourth soil engaging component comprising a fourth electrode of said electrode array; and
- an optical window located inline with said soil engaging components, and a sensor for measuring optical reflectance of the soil through said window.

22. The system according to claim 21, wherein said optical window and at least one of said second and third electrodes are attached to a runner assembly and arranged for sliding contact with the soil in said slot, said runner assembly being located inline with said electrode array between said first soil engaging component and said fourth soil engaging component.

23. A system for measuring pH of soil in a field, comprising:
- a narrow profile runner arranged to open a slot in the soil; and
- a pH sensor attached to said runner, said pH sensor comprising at least one ion-selective electrode and an actuator arranged to lower said electrode into contact with the soil in the slot to measure pH of the soil in situ.

24. The system according to claim 23, wherein said actuator comprises a linear actuator arranged to move said ion-selective electrode relative to said narrow profile runner to lower said ion-selective electrode into contact with a bottom surface of the slot to measure pH of the soil in situ.

25. The system according to claim 23, further comprising an optical window in a bottom surface of said runner for measuring optical reflectance of the soil through said window.

26. The system according to claim 25, further comprising at least one electrode arranged on a bottom side of said runner for sliding contact with the soil in said slot for measuring soil electrical conductivity or moisture.

27. The system according to claim 23, further comprising at least one electrode arranged on a bottom side of said runner for sliding contact with the soil in said slot for measuring soil electrical conductivity or moisture.

* * * * *